US012001756B2

(12) United States Patent
Liu et al.

(10) Patent No.: US 12,001,756 B2
(45) Date of Patent: *Jun. 4, 2024

(54) AUDIO PROCESSING DEVICE CAPABLE OF DYNAMICALLY SWITCHING COMPARISON CRITERION OF AUDIO DOSE

(71) Applicant: Realtek Semiconductor Corp., Hsinchu (TW)

(72) Inventors: Yu Wei Liu, Hsinchu (TW); Chi Wu, Hsinchu (TW); Chia Chun Hung, Hsinchu (TW)

(73) Assignee: Realtek Semiconductor Corp., Hsinchu (TW)

( * ) Notice: Subject to any disclaimer, the term of this patent is extended or adjusted under 35 U.S.C. 154(b) by 211 days.

This patent is subject to a terminal disclaimer.

(21) Appl. No.: 17/691,334

(22) Filed: Mar. 10, 2022

(65) Prior Publication Data

US 2023/0040518 A1 Feb. 9, 2023

(30) Foreign Application Priority Data

Aug. 6, 2021 (TW) .................................. 110129185

(51) Int. Cl.
*G06F 3/16* (2006.01)
*A61F 11/06* (2006.01)
(Continued)

(52) U.S. Cl.
CPC .............. *G06F 3/165* (2013.01); *H04R 1/08* (2013.01); *H04R 3/00* (2013.01); *A61F 11/06* (2013.01);
(Continued)

(58) Field of Classification Search
CPC .. G06F 3/165; H04R 1/08; H04R 3/00; H04R 2430/01; H04R 1/1041; H04R 2225/55;
(Continued)

(56) References Cited

U.S. PATENT DOCUMENTS

2008/0130906 A1* 6/2008 Goldstein .............. A61B 5/121
381/58
2008/0181442 A1 7/2008 Goldstein et al.
(Continued)

OTHER PUBLICATIONS

Taiwanese Notice of Allowance dated Jun. 1, 2022 for Application No. 110129185 with an English translation.
(Continued)

*Primary Examiner* — Carolyn R Edwards
*Assistant Examiner* — Kuassi A Ganmavo
(74) *Attorney, Agent, or Firm* — Birch, Stewart, Kolasch & Birch, LLP

(57) ABSTRACT

An audio processing device includes: a sound level measuring circuit arranged to operably generate multiple sound level values, wherein the multiple sound level values respectively correspond to the sound levels generated by an audio playback device at multiple time points or the sound levels received by a microphone at multiple time points; an audio dose calculating circuit coupled with the sound level measuring circuit and arranged to operably generate an audio dose value corresponding to a measuring period based on the multiple sound level values and contents of a weighting table; a control circuit coupled with the audio dose calculating circuit and arranged to operably compare the audio dose value with a dose threshold to determine whether to generate a control signal or not; and an indication signal generating circuit coupled with the control circuit and arranged to operably generate a corresponding indication signal according to the control signal.

8 Claims, 6 Drawing Sheets

(51) Int. Cl.
  *A61F 11/14* (2006.01)
  *G01H 3/12* (2006.01)
  *G10K 11/178* (2006.01)
  *H04R 1/08* (2006.01)
  *H04R 1/10* (2006.01)
  *H04R 3/00* (2006.01)
  *H04S 7/00* (2006.01)

(52) U.S. Cl.
  CPC .............. *A61F 11/145* (2022.01); *G01H 3/12* (2013.01); *G10K 11/1785* (2018.01); *G10K 2210/3056* (2013.01); *H04R 1/1041* (2013.01); *H04R 2225/55* (2013.01); *H04R 2420/01* (2013.01); *H04R 2430/01* (2013.01); *H04S 7/301* (2013.01); *H04S 2400/13* (2013.01)

(58) Field of Classification Search
  CPC ... H04R 25/407; H04S 7/301; H04S 2400/13; G10K 11/1785; G10K 2210/3056; G01H 3/12; G01H 3/14; A61F 11/06; A61F 11/145
  See application file for complete search history.

(56) References Cited

U.S. PATENT DOCUMENTS

| | | | | |
|---|---|---|---|---|
| 2008/0205660 | A1* | 8/2008 | Goldstein | G01H 3/14 381/60 |
| 2010/0141439 | A1* | 6/2010 | Lunner | G01H 3/14 340/540 |
| 2011/0281639 | A1* | 11/2011 | Porat | A63F 13/80 463/23 |
| 2012/0051555 | A1* | 3/2012 | Schevciw | H04R 1/1091 381/74 |
| 2012/0166377 | A1* | 6/2012 | Sathish | G06Q 10/00 706/47 |
| 2016/0126914 | A1* | 5/2016 | Voix | H03G 3/32 381/57 |
| 2016/0316303 | A1* | 10/2016 | Kornagel | G10L 21/0232 |
| 2017/0324390 | A1* | 11/2017 | Wheatley | H03G 9/025 |
| 2018/0343529 | A1* | 11/2018 | Lynch | H04R 3/00 |
| 2019/0385583 | A1* | 12/2019 | Muggleton | H04R 29/004 |

OTHER PUBLICATIONS

Taiwanese Office Action and Search Report for Taiwanese Application No. 110129187, dated Jun. 23, 2022, with English translation.
Taiwan Office Action for application No. 110129185 dated Jan. 24, 2022.
Taiwan Office Action for application No. 110129186 dated Jan. 24, 2022.
U.S. Office Action for U.S. Appl. No. 17/691,283, dated Jan. 16, 2024.

* cited by examiner

| SV (dB) | Weight Value |
|---|---|
| < 78 | 0 |
| 78 ~ 80 | 1 |
| 81 ~ 83 | 2 |
| 84 ~ 86 | 4 |
| 87 ~ 89 | 8 |
| 90 ~ 92 | 16 |
| 93 ~ 95 | 32 |
| 96 ~ 98 | 64 |
| 99 ~ 101 | 128 |
| 102 ~ 104 | 256 |
| 105 ~ 107 | 550 |
| 108 ~ 110 | 1100 |
| 111 ~ 113 | 2200 |
| 114 ~ 116 | 4200 |
| 117 ~ 119 | 8200 |
| 120 ~ 122 | 16400 |
| 123 ~ 125 | 32800 |

FIG. 2

| SV (dB) | Weight Value |
|---|---|
| < 78 | 0 |
| 78 ~ 80 | 1.1 |
| 81 ~ 83 | 2.2 |
| 84 ~ 86 | 4.4 |
| 87 ~ 89 | 8.8 |
| 90 ~ 92 | 17.6 |
| 93 ~ 95 | 35.2 |
| 96 ~ 98 | 70.4 |
| 99 ~ 101 | 140.8 |
| 102 ~ 104 | 281.6 |
| 105 ~ 107 | 605 |
| 108 ~ 110 | 1210 |
| 111 ~ 113 | 2420 |
| 114 ~ 116 | 4620 |
| 117 ~ 119 | 9020 |
| 120 ~ 122 | 18040 |
| 123 ~ 125 | 36080 |

FIG. 5

| SV (dB) | Weight Value |
|---|---|
| < 78 | 0 |
| 78 ~ 80 | 0.95 |
| 81 ~ 83 | 1.9 |
| 84 ~ 86 | 3.8 |
| 87 ~ 89 | 7.6 |
| 90 ~ 92 | 15.2 |
| 93 ~ 95 | 30.4 |
| 96 ~ 98 | 60.8 |
| 99 ~ 101 | 121.6 |
| 102 ~ 104 | 243.2 |
| 105 ~ 107 | 577.5 |
| 108 ~ 110 | 1155 |
| 111 ~ 113 | 2310 |
| 114 ~ 116 | 4410 |
| 117 ~ 119 | 8610 |
| 120 ~ 122 | 17220 |
| 123 ~ 125 | 34440 |

FIG. 6

AUDIO PROCESSING DEVICE CAPABLE OF DYNAMICALLY SWITCHING COMPARISON CRITERION OF AUDIO DOSE

CROSS-REFERENCE TO RELATED APPLICATIONS

This application claims the benefit of priority to Patent Application No. 110129185, filed in Taiwan on Aug. 6, 2021; the entirety of which is incorporated herein by reference for all purposes.

BACKGROUND

The disclosure generally relates to an audio dose monitoring technology and, more particularly, to an audio processing device and related audio dose monitoring circuit capable of dynamically switching comparison criterion of audio dose or capable of dynamically adjusting basis for calculating audio dose.

In daily life, work, or various entertainments, human ears often receive various sounds or noises. Many studies have shown that exposure to the loud environment or noise environment for too long can cause an adverse effect on the psychological or physiological levels of human beings. For example, it may cause symptoms such as tension, annoyance, and/or inattention, and it may also induce high blood pressure or temporary hearing loss, or even result in permanent hearing loss.

The World Health Organization (WHO) has issued a warning in 2019, pointing out that about 1.1 billion young people worldwide are at risk of hearing loss due to unsafe listening practice. Primary causes include frequent exposure to the loud volume of personal audio devices or frequent visits to noisy entertainment venues, or the like. However, modern people are using various consumer electronics or audio-visual equipment for more and more time, and as a result, more people are at risk of hearing loss and are not aware of it.

SUMMARY

An example embodiment of an audio processing device is disclosed, comprising: an audio playback device, arranged to operably generate sound based on an audio configuration signal; and an audio dose monitoring circuit, comprising: a sound level measuring circuit, arranged to operably generate multiple sound level values respectively corresponding to multiple sound levels based on the audio configuration signals, wherein the multiple sound levels are generated by the audio playback device at multiple time points; an audio dose calculating circuit, coupled with the sound level measuring circuit, and arranged to operably generate an audio dose value corresponding to a measuring period based on the multiple sound level values and contents of a weighting table; a control circuit, coupled with the audio dose calculating circuit, and arranged to operably generate the audio configuration signal, and to operably compare the audio dose value with a dose threshold to determine whether to generate a control signal or not; and an indication signal generating circuit, coupled with the control circuit, and arranged to operably generate a corresponding indication signal according to the control signal.

Another example embodiment of an audio processing device is disclosed, comprising: a microphone, arranged to operably receive sound; and an audio dose monitoring circuit, comprising: a sound level measuring circuit, arranged to operably generate multiple sound level values respectively corresponding to sound levels received by the microphone at multiple time points; an audio dose calculating circuit, coupled with the sound level measuring circuit, and arranged to operably generate an audio dose value corresponding to a measuring period based on the multiple sound level values and contents of a weighting table; a control circuit, coupled with the audio dose calculating circuit, and arranged to operably compare the audio dose value with a dose threshold to determine whether to generate a control signal or not; and an indication signal generating circuit, coupled with the control circuit, and arranged to operably generate a corresponding indication signal according to the control signal.

Another example embodiment of an audio dose monitoring circuit of an audio processing device is disclosed, comprising: a sound level measuring circuit, arranged to operably generate multiple sound level values respectively corresponding to multiple sound levels, wherein the multiple sound levels are generated by an audio playback device at multiple time points, or are received by a microphone at multiple time points; an audio dose calculating circuit, coupled with the sound level measuring circuit, and arranged to operably generate an audio dose value corresponding to a measuring period based on the multiple sound level values and contents of a weighting table; a control circuit, coupled with the audio dose calculating circuit, and arranged to operably compare the audio dose value with a dose threshold to determine whether to generate a control signal or not; and an indication signal generating circuit, coupled with the control circuit, and arranged to operably generate a corresponding indication signal according to the control signal.

Both the foregoing general description and the following detailed description are examples and explanatory only, and are not restrictive of the invention as claimed.

BRIEF DESCRIPTION OF THE DRAWINGS

FIG. 2 shows a simplified schematic diagram of a weighting table according to a first embodiment of the present disclosure.

FIG. 5 shows a simplified schematic diagram of a weighting table according to a third embodiment of the present disclosure.

FIG. 6 shows a simplified schematic diagram of a weighting table according to a fourth embodiment of the present disclosure.

DETAILED DESCRIPTION

Reference is made in detail to embodiments of the invention, which are illustrated in the accompanying drawings. The same reference numbers may be used throughout the drawings to refer to the same or like parts, components, or operations.

Figure 1:
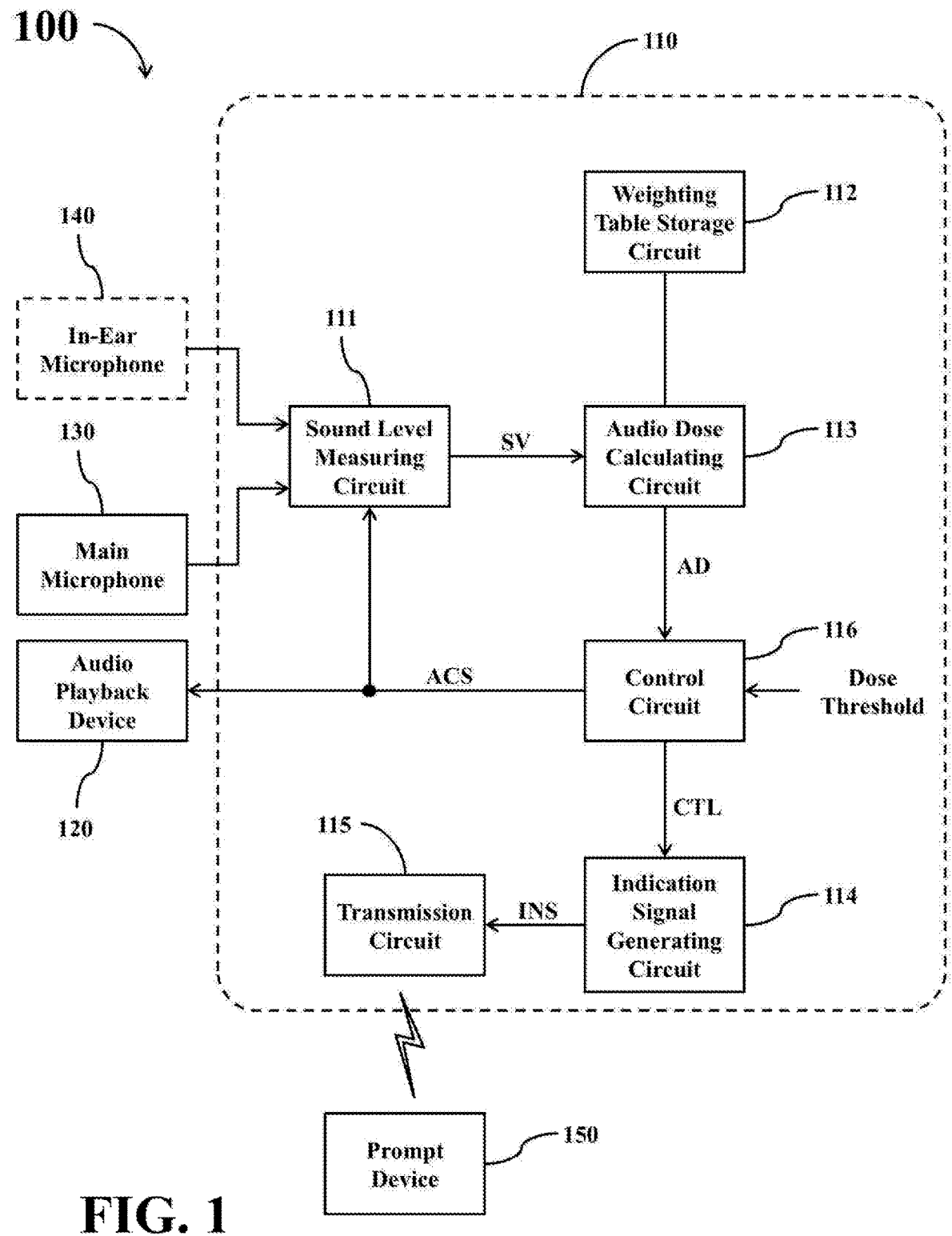
FIG. 1 shows a simplified functional block diagram of an audio processing device according to a first embodiment of the present disclosure.

FIG. 1 shows a simplified functional block diagram of an audio processing device 100 according to a first embodiment of the present disclosure. The audio processing device 100 comprises an audio dose monitoring circuit 110, an audio playback device 120, a main microphone 130, an in-ear microphone 140, and a prompt device 150. In the present embodiment, the audio dose monitoring circuit 110 comprises a sound level measuring circuit 111, a weighting table storage circuit 112, an audio dose calculating circuit 113, an indication signal generating circuit 114, a transmission circuit 115, and a control circuit 116.

In the audio processing device 100, the audio playback device 120 may be coupled with the audio dose monitoring circuit 110 by adopting various wired or wireless transmission approaches. The audio playback device 120 is arranged to operably generate or playback various sounds or music under the control of an audio configuration signal ACS generated by the audio dose monitoring circuit 110. In practice, the audio playback device 120 may be realized with various electronic devices capable of generating sound, such as wired earphones, wireless earphones, a wired speaker, a wireless speaker, a smart speaker, a smart TV, a desktop computer, a notebook computer, a tablet computer, a mobile phone, or the like.

The main microphone 130 is coupled with the audio dose monitoring circuit 110, and is arranged to operably receive sounds around the user to generate corresponding audio signals. The main microphone 130 may transmit the generated audio signals to the audio dose monitoring circuit 110 by adopting various wired transmission or wireless transmission approaches. If the audio processing device 100 has a voice communication functionality, then the main microphone 130 may be utilized as the user's voice input device.

The in-ear microphone 140 is coupled with the audio dose monitoring circuit 110, and may be placed inside the ear canal of the user for use. The in-ear microphone 140 is arranged to operably receive the sound coming into the ear canal of the user, so as to generate corresponding audio signals. Similarly, the in-ear microphone 140 may transmit the generated audio signals to the audio dose monitoring circuit 110 by adopting various wired transmission or wireless transmission approaches.

In practice, each of the main microphone 130 and the in-ear microphone 140 may be realized with various sound receiving devices capable of converting the received sound into an audio signal in analog format or in digital format.

The prompt device 150 is coupled with the audio dose monitoring circuit 110, and is arranged to operably generate appropriate prompt signals or prompt messages under the control of the audio dose monitoring circuit 110 or according to the instructions of the audio dose monitoring circuit 110. In practice, the prompt device 150 may be realized with various electronic devices capable of generating prompt signals or prompt messages, such as a buzzer, a speaker, a light emitting device, a display, a mobile phone, a desktop computer, a notebook computer, a tablet computer, a wearable device, or the like.

In the audio dose monitoring circuit 110, the sound level measuring circuit 111 is coupled with the main microphone 130, the in-ear microphone 140, and the control circuit 116. The sound level measuring circuit 111 is arranged to operably generate multiple sound level values SVs, wherein the multiple sound level values SVs respectively correspond to sound levels generated by the audio playback device 120 at multiple time points, sound levels received by the main microphone 130 at multiple time points, or sound levels received by the in-ear microphone 140 at multiple time points.

In operations, the sound level measuring circuit 111 may receive audio signals generated by the main microphone 130 by adopting various wired transmission or wireless transmission approaches, and may respectively convert the audio signals generated by the main microphone 130 at multiple time points into multiple first sound level values corresponding to the sound levels received by the main microphone 130 at the multiple time points.

Similarly, the sound level measuring circuit 111 may receive audio signals generated by the in-ear microphone 140 by adopting various wired transmission or wireless transmission approaches, and may respectively convert audio signals generated by the in-ear microphone 140 at multiple time points into multiple second sound level values corresponding to the sound levels received by the in-ear microphone 140 at the multiple time points.

In addition, the sound levels generated by the audio playback device 120 are determined by the audio configuration signal ACS generated by the control circuit 116. Therefore, the sound level measuring circuit 111 may respectively convert audio configuration signals ACSs generated by the control circuit 116 at multiple time points into multiple third sound level values corresponding to the sound levels generated by the audio playback device 120 at the multiple time points.

In one embodiment, the sound level measuring circuit 111 may decide a basis for calculating the sound level value SV based on a signal source pre-selected by a manufacturer of the audio dose monitoring circuit 110 or by a user of the audio dose monitoring circuit 110.

For example, if the pre-selected signal source is the audio playback device 120, then the sound level measuring circuit 111 may utilize the aforementioned multiple third sound level values to be multiple sound level values SVs corresponding to different sampling time points.

For another example, if the pre-selected signal source is the main microphone 130, then the sound level measuring circuit 111 may utilize the aforementioned multiple first sound level values to be multiple sound level values SVs corresponding to different sampling time points.

For another example, if the pre-selected signal source is the in-ear microphone 140, then the sound level measuring circuit 111 may utilize the aforementioned multiple second sound level values to be multiple sound level values SVs corresponding to different sampling time points.

In another embodiment, the sound level measuring circuit 111 may compare the magnitude of the first sound level value, the magnitude of the second sound level value, and the magnitude of the third sound level value corresponding to the same sampling time point, and may dynamically switch the basis for generating the sound level value SV according to the comparing results.

For example, if at a first sampling time point, the first sound level value is greater than the second sound level value and the third sound level value, then the sound level measuring circuit 111 may utilize the first sound level value to be a sound level value SV corresponding to the first sampling time point.

For another example, if at a second sampling time point, the third sound level value is greater than the first sound level value and the second sound level value, then the sound level measuring circuit 111 may utilize the third sound level value to be a sound level value SV corresponding to the second sampling time point.

For another example, if at a third sampling time point, the second sound level value is greater than the first sound level value and the third sound level value, then the sound level measuring circuit 111 may utilize the second sound level value to be a sound level value SV corresponding to the third sampling time point.

The sound level measuring circuit 111 may adopt the aforementioned method to dynamically decide the basis for generating sound level values SVs corresponding to other sampling time points.

In another embodiment, the sound level measuring circuit 111 may compare a spatial distance between the user and the main microphone 130, a spatial distance between the user and the in-ear microphone 140, and a spatial distance between the user and the audio playback device 120, and may dynamically switch the basis for generating the sound level value SV according to the comparing results.

For example, if at a first sampling time point, the sound level measuring circuit 111 determines that the audio playback device 120 is closer to the user than the main microphone 130 and the in-ear microphone 140, then the sound level measuring circuit 111 may utilize the third sound level value corresponding to the first sampling time point to be a sound level value SV corresponding to the first sampling time point.

For another example, if at a second sampling time point, the sound level measuring circuit 111 determines that the main microphone 130 is closer to the user than the audio playback device 120 and the in-ear microphone 140, then the sound level measuring circuit 111 may utilize the first sound level value corresponding to the second sampling time point to be a sound level value SV corresponding to the second sampling time point.

For another example, if at a third sampling time point, the sound level measuring circuit 111 determines that the in-ear microphone 140 is closer to the user than the audio playback device 120 and the main microphone 130, then the sound level measuring circuit 111 may utilize the second sound level value corresponding to the third sampling time point to be a sound level value SV corresponding to the third sampling time point.

The sound level measuring circuit 111 may adopt the aforementioned method to dynamically decide the basis for generating sound level values SVs corresponding to other sampling time points.

In practice, the sound level measuring circuit 111 may generate a sound level value SV every once in a certain period of time (e.g., every 0.1 second, every 0.25 second, every 0.3 second, every 0.5 second, every 0.6 second, every second, every 1.5 seconds, every two seconds, every three seconds, or the like), and may utilize various appropriate data formats to present the magnitude of the sound level value SV, such as Pa, μPa, dB (decibel), or the like. The length of the interval between two consecutive sound level values SVs generated by the sound level measuring circuit 111 is hereinafter referred to as a unit time length.

As can be appreciated from the foregoing descriptions, if the unit time length is one second, then the sound level measuring circuit 111 would generate 60 sound level values SVs within one minute, and would generate 3600 sound level values SVs within one hour. If the unit time length is two seconds, then the sound level measuring circuit 111 would generate 30 sound level values SVs within one minute, and would generate 1800 sound level values SVs within one hour.

In the audio dose monitoring circuit 110, the weighting table storage circuit 112 is arranged to operably store one or more weighting tables, wherein each weighting table is recorded with the mapping relationship between sound levels and weight values. For example, FIG. 2 shows a simplified schematic diagram of a weighting table 200 according to a first embodiment of the present disclosure. In the weighting table 200, the sound level value is presented as dB (decibel).

As shown in FIG. 2, the mapping relationship between the sound levels and the weight values is stepwise. The weight values corresponding to respective sound levels to some extent represent a risk of hearing loss that may be caused by exposure to respective sound levels. In the embodiment of FIG. 2, each time the magnitude of sound level value increases by one level (about 3 dB), the corresponding weight value doubles (or about double).

The audio dose calculating circuit 113 is coupled with the sound level measuring circuit 111 and the weighting table storage circuit 112, and is arranged to operably generate an audio dose value AD corresponding to a measuring period based on the multiple sound level values SVs generated by the sound level measuring circuit 111 and the contents of a specific weighting table. The aforementioned measuring period may be configured to various appropriate time lengths, such as fifteen minutes, twenty minutes, thirty minutes, one hour, two hours, three hours, five hours, eight hours, twelve hours, one day, three days, seven days, or the like.

In operations, the audio dose calculating circuit 113 may respectively convert the multiple sound level values SVs into corresponding multiple weight values based on the contents of the specific weighting table, and may respectively multiply the multiple weight values by multiple corresponding unit time lengths, so as to generate multiple weighted values, wherein a sum of the aforementioned multiple unit time lengths equals a total time length of the aforementioned measuring period.

Then, the audio dose calculating circuit 113 may calculate a sum of the aforementioned multiple weighted values, and utilizes the sum to be an audio dose value AD corresponding to the measuring period.

If the sound level SV received by the audio dose calculating circuit 113 at a first time point is 80 dB, then the audio dose calculating circuit 113 may convert the sound level value SV into a corresponding weight value "1" based on the contents of the weighting table 200.

If the sound level SV received by the audio dose calculating circuit 113 at a second time point is 91 dB, then the audio dose calculating circuit 113 may convert the sound level value SV into a corresponding weight value "16" based on the contents of the weighting table 200.

If the sound level SV received by the audio dose calculating circuit 113 at a third time point is 65 dB, then the audio dose calculating circuit 113 may convert the sound level value SV into a corresponding weight value "0" based on the contents of the weighting table 200.

If the sound level SV received by the audio dose calculating circuit 113 at a fourth time point is 114 dB, then the audio dose calculating circuit 113 may convert the sound level value SV into a corresponding weight value "4200" based on the contents of the weighting table 200.

For example, it is assumed that the aforementioned measuring period is one hour, and the unit time length (i.e., the time length of the interval between two consecutive sound level values SVs generated by the sound level measuring circuit 111) is one second. In this situation, the audio dose calculating circuit 113 would receive 3600 sound level values SVs within one hour. For simplifying the description, it is assumed hereinafter that among the aforementioned 3600 sound level values SVs, the magnitudes of 1200 sound level values SVs are 60 dB, the magnitudes of 1800 sound level values SVs are 85 dB, and the magnitudes of 600 sound level values SVs are 100 dB.

In this situation, the audio dose calculating circuit 113 may respectively convert the 1200 sound level values SVs whose magnitude are 60 dB into corresponding 1200 weight values "0", may respectively convert the 1800 sound level values SVs whose magnitude are 85 dB into corresponding 1800 weight values "4", and may respectively convert the 600 sound level values SVs whose magnitude are 100 dB into corresponding 600 weight values "128" based on the contents of the weighting table 200.

In addition, the audio dose calculating circuit 113 may respectively multiply the aforementioned 1200 weight values "0" by the unit time length "1" to generate 1200 weighted values "0", may respectively multiply the aforementioned 1800 weight values "4" by the unit time length "1" to generate 1800 weighted values "4", and may respectively multiply the aforementioned 600 weight values "128" by the unit time length "1" to generate 600 weighted values "128".

Then, the audio dose calculating circuit 113 may calculate a sum of the aforementioned multiple weighted values (in this case it would be 84000=0*1200+4*1800+128*600), and may utilize the resulting sum to be the audio dose value AD corresponding to the recent one hour.

For another example, it is assumed hereinafter that the aforementioned measuring period is thirty minutes, and the unit time length (i.e., the time length of the interval between two consecutive sound level values SVs generated by the sound level measuring circuit 111) is two seconds. In this situation, the audio dose calculating circuit 113 would receive 900 sound level values SVs within thirty minutes. For simplifying the description, it is assumed hereinafter that among the aforementioned 900 sound level values SVs, the magnitudes of 100 sound level values SVs are 55 dB, the magnitudes of 300 sound level values SVs are 82 dB, the magnitudes of 270 sound level values SVs are 88 dB, and the magnitudes of 230 sound level values SVs are 94 dB.

In this situation, the audio dose calculating circuit 113 may respectively convert the 100 sound level values SVs whose magnitude are 55 dB into corresponding 100 weight values "0", may respectively convert the 300 sound level values SVs whose magnitude are 82 dB into corresponding 300 weight values "2", may respectively convert the 270 sound level values SVs whose magnitude are 88 dB into corresponding 270 weight values "8", and may respectively convert the 230 sound level values SVs whose magnitude are 94 dB into corresponding 230 weight values "32" based on the contents of the weighting table 200.

In addition, the audio dose calculating circuit 113 may respectively multiply the aforementioned 1200 weight values "0" by the unit time length "2" to generate 1200 weighted values "0", may respectively multiply the aforementioned 300 weight values "2" by the unit time length "2" to generate 300 weighted values "4", may respectively multiply the aforementioned 270 weight values "8" by the unit time length "2" to generate 270 weighted values "16", and may respectively multiply the aforementioned 230 weight values "32" by the unit time length "2" to generate 230 weighted values "64".

Then, the audio dose calculating circuit 113 may calculate a sum of the aforementioned multiple weighted values (in this case it would be 20240=0*100+4*300+16*270+64*230), and may utilize the resulting sum to be the audio dose value AD corresponding to the recent thirty minutes.

In practice, the audio dose calculating circuit 113 may adopt the aforementioned method to utilize a sum of weighted values with respect to a specific measuring period to be the audio dose value AD, and may transmit the audio dose value AD to the control circuit 116 after the measuring period.

Alternatively, the audio dose calculating circuit 113 may calculate a moving sum of weighted values with respect to a specific measuring period on a rolling basis, and may utilize the resulting moving sum to be the audio dose value AD.

As shown in FIG. 1, the control circuit 116 is coupled with the audio dose calculating circuit 113, the indication signal generating circuit 114, and the audio playback device 120. The control circuit 116 is arranged to operably generate an audio configuration signal ACS for controlling the audio playback device 120. In addition, the control circuit 116 may transmit the generated audio configuration signal ACS to the audio playback device 120 by adopting various wired transmission or wireless transmission approaches. As described previously, the audio playback device 120 may generate or playback various sounds or music under the control of the audio configuration signal ACS.

In addition, the control circuit 116 is further arranged to operably compare the audio dose value AD with a dose threshold to determine whether to generate a control signal CTL or not.

The magnitude of the dose threshold is related to the length of the aforementioned measuring period. In one embodiment, for example, if the measuring period is seven days, then the control circuit 116 may configure the dose threshold to be 144000; if the measuring period is one day, then the control circuit 116 may configure the dose threshold to be 20571; if the measuring period is one hour, then the control circuit 116 may configure the dose threshold to be 857; and so forth.

If the audio dose value AD exceeds a corresponding dose threshold, then the control circuit 116 may determine that the audio dose received by the user in the aforementioned measuring period has reached the point that is harmful to the user's hearing health. In this situation, the control circuit 116 generates and transmits a control signal CTL to the indication signal generating circuit 114.

The indication signal generating circuit 114 is arranged to operably generate a corresponding indication signal INS based on the control signal CTL generated by the control circuit 116.

The transmission circuit 115 is coupled with the indication signal generating circuit 114, and is arranged to operably transmit the indication signal INS to the prompt device 150 by adopting various wired or wireless transmission approaches, so that the prompt device 150 generates corresponding prompt signals or prompt messages accordingly to inform the user of that the audio dose exposure has reached a warning level. For example, the prompt device 150 may generate various warning lights, warning sounds, warning music, warning voices, reminding texts, and/or reminding images according to the indication signal INS to remind the user to take relevant protective measures.

In some embodiments, the control circuit 116 may further proactively adjust the audio configuration signal ACS to turn down the volume of sounds or music generated by the audio playback device 120 in the situation where the audio dose value AD exceeds the dose threshold.

In practice, the aforementioned sound level measuring circuit 111 may be realized with various appropriate circuits or chips having signal reception capabilities, signal processing capabilities, and signal conversion capabilities. The weighting table storage circuit 112 may be realized with various volatile memories or non-volatile storage devices. The audio dose calculating circuit 113 may be realized with various micro-processors, micro-controllers, digital processing circuits, digital signal processing circuits, or ASICs (Application Specific Integrated Circuits). The indication signal generating circuit 114 may be realized with various appropriate circuits having command processing capabilities and signal generating capabilities. The transmission circuit 115 may be realized with various wired or wireless transmission interfaces. For example, depending on the communication approach utilized for communicating with the prompt device 150, the transmission circuit 115 may be realized with a signal cable, an I2S (Inter-IC Sound) interface, a USB (Universal Serial Bus) interface, a UART (Universal Asynchronous Receiver/Transmitter) interface, a SATA (Serial Advanced Technology Attachment) interface, a PCI (Peripheral Component Interconnect) interface, a PCI-E (Peripheral Component Interconnect Express) interface, a NIC (Network Interface Card) interface, a Wi-Fi interface, a Bluetooth interface, a BLE (Bluetooth Low Energy) interface, a NFC (Near Field Communication) interface, or a combination of multiple aforementioned interfaces. The control circuit 116 may be realized with various micro-processors, micro-controllers, digital processing circuits, digital signal processing circuits, or ASICs.

Different functional blocks of the aforementioned audio dose monitoring circuit 110 may be respectively realized with separate circuits, or may be integrated into a single circuit chip. For example, the sound level measuring circuit 111 may be integrated with the audio dose calculating circuit 113. For another example, the audio dose calculating circuit 113 may be integrated with the control circuit 116. For another example, the indication signal generating circuit 114 may be integrated with the control circuit 116.

In practice, the audio dose monitoring circuit 110 and the audio playback device 120 may be integrated into a single device. Alternatively, the audio dose monitoring circuit 110 and the prompt device 150 may be integrated into a single device.

As can be appreciated from the foregoing descriptions, the audio dose monitoring circuit 110 may measure the sound level generated by the audio playback device 120, the sound level received by the main microphone 130, and the sound level received by the in-ear microphone 140, and the audio dose monitoring circuit 110 may generate audio dose values AD corresponding to the measuring results. When the audio dose monitoring circuit 110 determines that the audio dose value AD exceeds a predetermined threshold, the audio dose monitoring circuit instructs the prompt device 150 to generate relevant prompt signals or prompt messages, so that the user can be informed of the monitoring results of the audio dose monitoring circuit 110.

In practical applications, as long as the audio dose monitoring circuit 110 is integrated into various audio processing devices 100 that users often use, the audio dose received by the user can be measured and monitored at any time.

Another advantage of the aforementioned audio processing device 100 is that the audio dose monitoring circuit 110 can automatically generate relevant prompt signals when the audio dose received by the user exceeds a predetermined standard to remind the user to take relevant protective measures. As a result, it can effectively reduce the user's risk of hearing loss.

Different users have different physiological characteristics and physiological conditions, so their sensitivity and/or tolerance to the received audio dose may vary. In addition, in some applications, the audio processing device 100 may be used by a single user only, whereas in other applications, the audio processing device 100 may be used by multiple users (e.g., multiple family members or multiple colleagues) in turn.

Therefore, in some embodiments, the control circuit 116 is further arranged to operably switch a magnitude of the aforementioned dose threshold when a predetermined criterion is met. That is, the control circuit 116 is further arranged to operably switch a comparison criterion of the audio dose value AD generated by the audio dose calculating circuit 113.

In one embodiment, the aforementioned predetermined criterion refers to that an age of the user of the audio processing device 100 is over a predetermined age. In operations, the control circuit 116 may configure different audio dose comparison criteria for different age groups. For example, for users younger than 15 years old, the control circuit 116 may configure the comparison criterion of the audio dose value AD as a first dose threshold TH1; for users between the ages of 15 and 20 years old, the control circuit 116 may configure the comparison criterion of the audio dose value AD as a second dose threshold TH2; for users between the ages of 20 and 30 years old, the control circuit 116 may configure the comparison criterion of the audio dose value AD as a third dose threshold TH3; for users older than 30 years old, the control circuit 116 may configure the comparison criterion of the audio dose value AD as a fourth dose threshold TH4.

In some applications that pay more attention on the user's hearing health or physical and mental health, the control circuit 116 may configure the aforementioned second dose threshold TH2 to be greater than the first dose threshold TH1, configure the third dose threshold TH3 to be greater than the second dose threshold TH2, and configure the fourth dose threshold TH4 to be greater than the third dose threshold TH3.

In some applications that pay more attention on the user's entertainment experience, the control circuit 116 may configure the aforementioned fourth dose threshold TH4 to be greater than the first dose threshold TH1, configure the second dose threshold TH2 to be greater than the fourth dose threshold TH4, and configure the third dose threshold TH3 to be greater than the second dose threshold TH2.

As a result, the control circuit 116 would automatically switch the magnitude of the aforementioned dose threshold in the situation where the age of the user of the audio processing device 100 is over a predetermined age (e.g., age of 15).

In practice, the control circuit 116 may cooperate with various appropriate mechanisms to determine the user's age. For example, in the embodiment where the prompt device 150 is realized with a mobile phone, a desktop computer, a notebook computer, a tablet computer, or a wearable device, the control circuit 116 may request the user to input basic information, e.g., age, or the like, through the prompt device 150 in advance. For another example, the control circuit 116 may request the user to provide basic information, e.g., age, or the like, through other input devices (not illustrated in drawings) in advance. For another example, the control circuit 116 may cooperate with various image capture circuits having face recognition capability (not illustrated in drawings) to automatically estimate the user's age.

In another embodiment, the aforementioned predetermined criterion refers to that a predetermined physiological indicator of the user of the audio processing device 100 exceeds a predetermined degree. For example, the control circuit 116 may configure the aforementioned dose threshold as a first dose threshold TH1 when the user's heart rate or blood pressure is normal, and switch the aforementioned dose threshold from the first dose threshold TH1 to a different second dose threshold TH2 when the user's heart rate or blood pressure increases by more than 20%. The control circuit 116 may switch the aforementioned dose threshold from the second dose threshold TH2 to a different third dose threshold TH3 when the user's heart rate or blood pressure increases by more than 40%.

For another example, the control circuit 116 may configure the aforementioned dose threshold as a first dose threshold of TH1 when the user's breathing rate is normal, and switch the aforementioned dose threshold from the first dose threshold TH1 to a different second dose threshold TH2 when the user's breathing rate increases by more than 15%. The control circuit 116 may switch the aforementioned dose threshold from the second dose threshold TH2 to a different third dose threshold TH3 when the user's breathing rate increases by more than 50%.

In some applications, the control circuit 116 may configure the aforementioned second dose threshold TH2 to be smaller than the first dose threshold TH1, and configure the third dose threshold TH3 to be smaller than the second dose threshold TH2.

In practice, the control circuit 116 may adopt various appropriate mechanisms or cooperate with various appropriate detection devices to detect the user's predetermined physiological indicators. For example, in the embodiment where the prompt device 150 is realized with a wearable device, the control circuit 116 may utilize the prompt device 150 to detect the user's predetermined physiological indicators. For another example, the control circuit 116 may cooperate with various physiological index tracking devices having physiological indicator detecting capability (not illustrated in drawings) to track the change in the user's predetermined physiological indicators.

In another embodiment, the aforementioned predetermined criterion refers to that the user of the audio processing device 100 is on a menstrual period. For example, the control circuit 116 may switch the aforementioned dose threshold from a first dose threshold TH1 to a different second dose threshold TH2 when the user is on the menstrual period. The control circuit 116 may switch the aforementioned dose threshold from the second dose threshold TH2 back to the original first dose threshold TH1 after the user's menstrual period ends. In some applications, the control circuit 116 may configure the aforementioned second dose threshold TH2 to be smaller than the first dose threshold TH1.

In practice, the control circuit 116 may cooperate with various appropriate mechanisms to determine whether the user is on the menstrual period or not. For example, in the embodiment where the prompt device 150 is realized with a mobile phone, a desktop computer, a notebook computer, a tablet computer, or a wearable device, the control circuit 116 may request the user to provide her menstrual period data through the prompt device 150 in advance. Alternatively, the control circuit 116 may request the user to provide her menstrual period data through other input devices (not illustrated in drawings) in advance.

In another embodiment, the aforementioned predetermined criterion refers to that the user of the audio processing device 100 is on a gestation period. For example, the control circuit 116 may switch the aforementioned dose threshold from a first dose threshold TH1 to a different third dose threshold TH3 when the user is on the gestation period. The control circuit 116 may switch the aforementioned dose threshold from the third dose threshold TH3 back to the original first dose threshold TH1 after the user gives birth. In some applications, the control circuit 116 may configure the aforementioned third dose threshold TH3 to be smaller than the first dose threshold TH1.

In practice, the control circuit 116 may cooperate with various appropriate mechanisms to determine whether the user is on the gestation period or not. For example, in the embodiment where the prompt device 150 is realized with a mobile phone, a desktop computer, a notebook computer, a tablet computer, or a wearable device, the control circuit 116 may request the user to provide the date of pregnancy and childbirth through the prompt device 150. Alternatively, the control circuit 116 may request the user to provide the date of pregnancy and childbirth through other input devices (not illustrated in drawings).

In another embodiment, the aforementioned predetermined criterion refers to that an operating time of the audio processing device 100 is nighttime. For example, the control circuit 116 may configure the aforementioned dose threshold as a first dose threshold TH1 when the operating time of the audio processing device 100 is daytime, and switch the aforementioned dose threshold from the first dose threshold TH1 to a different second dose threshold TH2 when the operating time of the audio processing device 100 is nighttime. The control circuit 116 may configure the relative magnitude between the aforementioned second dose threshold TH2 and first dose threshold TH1 based on the design requirements of the application purpose.

In practice, the control circuit 116 may adopt various appropriate mechanisms or cooperate with various appropriate devices to determine the operating time of the audio processing device 100. For example, in the embodiment where the audio dose monitoring circuit 110 has a built-in clock (not illustrated in drawings), the control circuit 116 may utilize the built-in clock to determine the operating time of the audio processing device 100. For another example, in the embodiment where the prompt device 150 is realized with a mobile phone, a desktop computer, a notebook computer, a tablet computer, or a wearable device, the control circuit 116 may utilize the prompt device 150 to verify the operating time of the audio processing device 100. For another example, the control circuit 116 may utilize other devices to connect to the Internet to inquire the current time at the geographical location of the audio dose monitoring circuit 110.

In another embodiment, the aforementioned predetermined criterion refers to that an environmental temperature of the audio processing device 100 exceeds a predetermined magnitude. For example, the control circuit 116 may configure the aforementioned dose threshold as a first dose threshold TH1 when the environmental temperature of the audio processing device 100 is normal, and switch the aforementioned dose threshold from the first dose threshold TH1 to a different second dose threshold TH2 when the environmental temperature of the audio processing device 100 increases by more than 10%. The control circuit 116 may switch the aforementioned dose threshold from the second dose threshold TH2 to a different third dose threshold TH3 when the environmental temperature of the audio processing device 100 increases by more than 20%. In some applications, the control circuit 116 may configure the aforementioned second dose threshold TH2 to be smaller than the first dose threshold TH1, and configure the third dose threshold TH3 to be smaller than the second dose threshold TH2.

For another example, the control circuit 116 may switch the aforementioned dose threshold from the first dose threshold TH1 to a different second dose threshold TH2 when the environmental temperature of the audio processing device 100 drops by more than 10%. The control circuit 116 may switch the aforementioned dose threshold from the second dose threshold TH2 to a different third dose threshold TH3 when the environmental temperature of the audio processing device 100 drops by more than 20%. In some applications, the control circuit 116 may configure the aforementioned second dose threshold TH2 to be greater than the first dose threshold TH1, and configure the third dose threshold TH3 to be greater than the second dose threshold TH2.

In practice, the control circuit 116 may adopt various appropriate mechanisms or cooperate with various appropriate detection devices to detect the environmental temperature of the audio processing device 100. For example, in the embodiment where the audio dose monitoring circuit 110 has a built-in temperature sensor (not illustrated in drawings), the control circuit 116 may utilize the built-in temperature sensor to detect the environmental temperature of the audio processing device 100. For another example, in the embodiment where the prompt device 150 is realized with a wearable device, the control circuit 116 may utilize the prompt device 150 to detect the environmental temperature of the audio processing device 100. For another example, the control circuit 116 may utilize other devices to connect to the Internet to inquire the current environmental temperature of the geographical location of the audio dose monitoring circuit 110.

In another embodiment, the aforementioned predetermined criterion refers to that the user of the audio processing device 100 has changed, and the age difference between a new user and an original user exceeds a predetermined value. For example, the control circuit 116 may switch the aforementioned dose threshold from a first dose threshold TH1 to a different second dose threshold TH2 when the new user is more than five years older than the original user.

For another example, the control circuit 116 may switch the aforementioned dose threshold from the first dose threshold TH1 to a different third dose threshold TH3 when the new user is more than fifteen years older than the original user.

For another example, the control circuit 116 may switch the aforementioned dose threshold from the first dose threshold TH1 to a different fourth dose threshold TH4 when the new user is more than ten years younger than the original user.

The control circuit 116 may configure the relative magnitude among the aforementioned first dose threshold TH1, second dose threshold TH2, third dose threshold TH3, and fourth dose threshold TH4 based on the design requirements of the application purpose.

In practice, the control circuit 116 may cooperate with various appropriate detecting mechanisms or identity authentication mechanisms to determine whether the user of the audio processing device 100 has changed or not. For example, the control circuit 116 may cooperate with various iris recognition devices (not illustrated in drawings), fingerprint identification devices (not illustrated in drawings), or face recognition devices (not illustrated in drawings) to determine whether the user of the audio processing device 100 has changed or not. For another example, the control circuit 116 may request the user to input information, e.g., an identification code or a password, or the like, through other input devices (not illustrated in drawings), so that the control circuit 116 can determine whether the user of the audio processing device 100 has changed accordingly.

As described previously, the control circuit 116 may adopt aforementioned various approaches to determine the ages of the original user and the new user. For the sake of brevity, those descriptions will not be repeated here.

In another embodiment, the aforementioned predetermined criterion refers to that the user of the audio processing device 100 has changed, and the sex of a new user is different from the sex of an original user. For example, the control circuit 116 may switch the aforementioned dose threshold from a first dose threshold TH1 to a different second dose threshold TH2 when the user of the audio processing device 100 changes from a male user to a female user.

For another example, the control circuit 116 may switch the aforementioned dose threshold from a second dose threshold TH2 to a different first dose threshold TH1 when the user of the audio processing device 100 changes from a female user to a male user.

The control circuit 116 may configure the relative magnitude between the aforementioned first dose threshold TH1 and second dose threshold TH2 based on the design requirements of the application purpose.

In practice, the control circuit 116 may adopt aforementioned various approaches to determine whether the sex of the user of the audio processing device 100 has changed or not. For the sake of brevity, those descriptions will not be repeated here.

In some embodiments, the control circuit 116 may switch the magnitude of the dose threshold (i.e., switch the comparison criterion of the audio dose value AD) when any one of the aforementioned predetermined criteria is met.

In other embodiments, the control circuit 116 switches the magnitude of the dose threshold only when two or more than two of the aforementioned predetermined criteria are met.

As can be appreciated from the foregoing descriptions, the control circuit 116 may adaptively switch the magnitude of the dose threshold utilized to compare with the audio dose value AD generated by the audio dose calculating circuit 113 based on differences in the user's own physiological condition, differences between users, differences in environmental temperature, and/or differences in time of use. Such approach not only significantly improves the flexibility of use and the application scope of the audio dose monitoring circuit 110, but also renders the audio dose monitoring circuit 110 and the audio processing device 100 to better meet the needs of different users, and/or different usage scenarios.

From another aspect, the aforementioned structure and operations of the audio dose monitoring circuit 110 can offer the user an adaptive hearing protection that is more customized and can be automatically adapted in response to different conditions.

In addition, the aforementioned structure and operations of the audio dose monitoring circuit 110 can also enable the audio processing device 100 to support applications shared by multiple users, which significantly increases the application value of the audio processing device 100.

Figure 3:
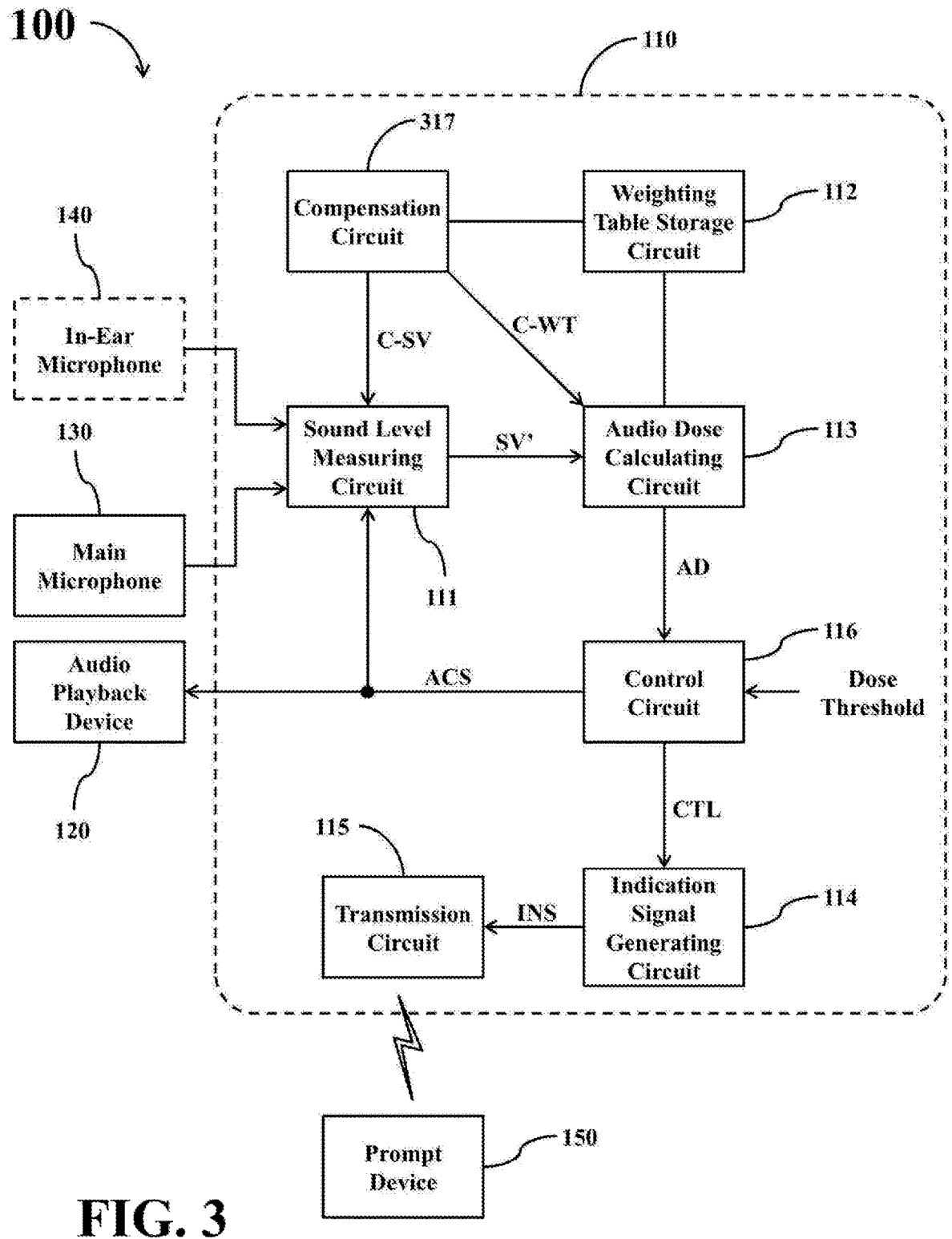
FIG. 3 shows a simplified functional block diagram of an audio processing device according to a second embodiment of the present disclosure.

Please refer to FIG. 3, which shows a simplified functional block diagram of an audio processing device 100 according to a second embodiment of the present disclosure.

Comparing with the aforementioned embodiment of FIG. 1, the audio dose monitoring circuit 110 in FIG. 3 further comprises a compensation circuit 317. As shown in FIG. 3, the compensation circuit 317 is coupled with the sound level measuring circuit 111 and arranged to operably compensate multiple sound level values SVs generated by the sound level measuring circuit 111 when a first target criterion is met.

In one embodiment, the aforementioned first target criterion refers to that the audio playback device 120 is equipped with a passive noise suppression structure (not illustrated in drawings). As described previously, the audio playback device 120 may be realized with wired earphones or wireless earphones, and the sound level measuring circuit 111 may generate sound level values SVs of respective sampling time points by adopting aforementioned various approaches.

In practical applications, the audio playback device 120 may be equipped with various passive noise suppression structures to improve the sound field effect of the audio playback device 120. For example, the audio playback device 120 may be equipped with a headphone cover structure having better coverage, earcup washers with better sound-absorption capability, or a thicker headphone cover, or that the shape of the main body of the audio playback device 120 may be designed to better fit the shape of the ear canal.

Because of the aforementioned various passive noise suppression structures, the sound level received by the user when the user puts on the audio playback device 120 would be lower than the actual sound level of the external environment, and thus the user may not realize that he or she is actually exposed to an unhealthy loud environment, such as noisy entertainment venues, bars, stadiums, or the like.

Therefore, in the situation where the audio playback device 120 is equipped with the passive noise suppression structure, the compensation circuit 317 may instruct the sound level measuring circuit 111 to compensate the sound level values SVs of respective sampling time points according to a noise suppression effect generated by the aforementioned passive noise suppression structure.

For example, if the noise suppression effect generated by the aforementioned passive noise suppression structure is −5 dB, then the compensation circuit 317 may generate and transmit a sound level compensating value C-SV to the sound level measuring circuit 111, so as to instruct the sound level measuring circuit 111 to add a compensation amount of 3-5 dBs to each sound level value SV to form a compensated sound level value SV'.

For another example, if the noise suppression effect generated by the aforementioned passive noise suppression structure is −10 dB, then the compensation circuit 317 may generate and transmit a sound level compensating value C-SV to the sound level measuring circuit 111, so as to instruct the sound level measuring circuit 111 to add a compensation amount of 8-10 dBs to each sound level value SV to form a compensated sound level value SV'.

In another embodiment, the aforementioned first target criterion refers to that the audio playback device 120 has an ANC (active noise cancellation) functionality. As described previously, the audio playback device 120 may be realized with wired earphones or wireless earphones. As is well known in related art, some earphones have the ANC functionality, which can improve the sound field effect of the audio playback device 120.

Similarly, the aforementioned ANC functionality renders the sound level received by the user when the user puts on the audio playback device 120 to be lower than the actual sound level of the external environment, and thus the user may not realize that he or she is actually exposed to an unhealthy loud environment, such as noisy entertainment venues, bars, stadiums, or the like.

Therefore, in the situation where the audio playback device 120 has the ANC functionality, the compensation circuit 317 may instruct the sound level measuring circuit 111 to compensate the sound level values SVs of respective sampling time points according to the noise suppression effect generated by the aforementioned ANC functionality.

For example, if the noise suppression effect generated by the aforementioned ANC functionality is −15 dB, then the compensation circuit 317 may generate and transmit a sound level compensating value C-SV to the sound level measuring circuit 111, so as to instruct the sound level measuring circuit 111 to add a compensation amount of 12-15 dBs to each sound level value SV to form a compensated sound level value SV'.

For another example, if the noise suppression effect generated by the aforementioned ANC functionality is −30 dB, then the compensation circuit 317 may generate and transmit a sound level compensating value C-SV to the sound level measuring circuit 111, so as to instruct the sound level measuring circuit 111 to add a compensation amount of 25-30 dBs to each sound level value SV to form a compensated sound level value SV'.

Then the audio dose calculating circuit 113 may adopt the method of the embodiment of FIG. 1 as elaborated above to utilize the compensated sound level value SV' to calculate the corresponding audio dose value AD.

Therefore, the compensation performed by the aforementioned compensation circuit 317 on the sound level value SV generated by the sound level measuring circuit 111 in the situation where the first target criterion is met is equivalent to adjusting the basis for calculating the audio dose value AD.

In practice, the compensation circuit 317 may instruct the sound level measuring circuit 111 to compensate the generated sound level values SVs (i.e., to adjust the basis for calculating the audio dose value AD) when any one of the aforementioned first target criteria is met.

In other embodiments, the compensation circuit 317 instructs the sound level measuring circuit 111 to compensate the multiple sound level values SVs generated by the sound level measuring circuit 111 only when two of the aforementioned first target criteria are met.

As described previously, the audio processing device 100 may be used by a single user only, whereas in other applications, the audio processing device 100 may be used by multiple users (e.g., multiple family members or multiple colleagues) in turn. Different users have different physiological characteristics and physiological conditions, so their sensitivity and/or tolerance to the received audio dose may vary.

In the embodiment of FIG. 3, the compensation circuit 317 is further coupled with the weighting table storage circuit 112 and the audio dose calculating circuit 113, and is arranged to operably adjust the contents of a weighting table utilized by the audio dose calculating circuit 113 when a second target criterion is met.

In one embodiment, the aforementioned second target criterion refers to that the user of the audio processing device 100 is over a predetermined age. In practice, the compensation circuit 317 may configure different weighting tables for different age groups, and may instruct the audio dose calculating circuit 113 to utilize corresponding weighting table according to the age of the user, that is, to adjust the contents of the weighting table utilized by the audio dose calculating circuit 113.

For example, the compensation circuit 317 may configure a corresponding first weighting table (e.g., the weighting table 200 shown in FIG. 2) for users between the ages of 20 and 30 years old.

Figure 4:
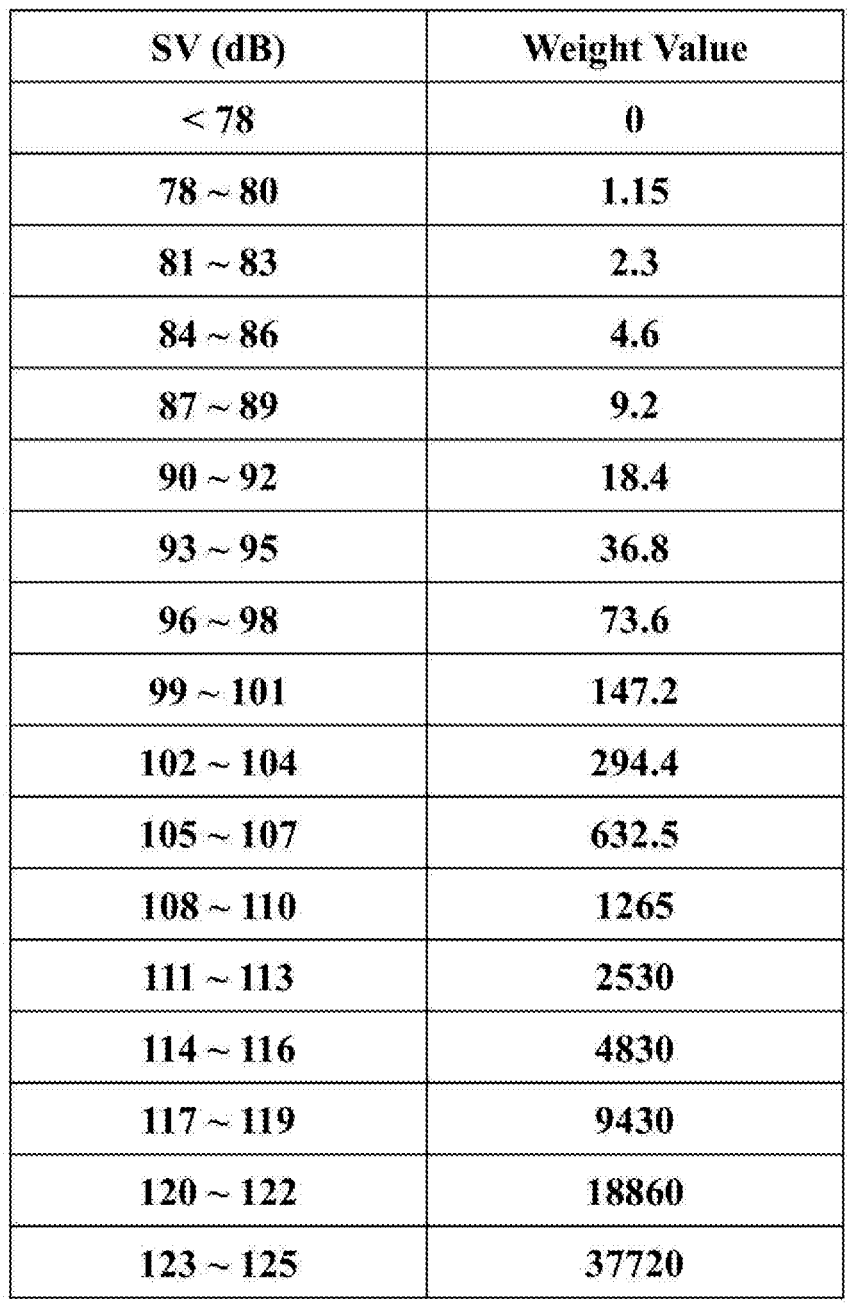
FIG. 4 shows a simplified schematic diagram of a weighting table according to a second embodiment of the present disclosure.

For another example, the compensation circuit 317 may configure a corresponding second weighting table (e.g., a weighting table 400 shown in FIG. 4) whose weight values are higher than that of the first weighting table for users younger than 15 years old. In the embodiment of FIG. 4, weight values corresponding to respective sound level values in the weighting table 400 increase by 15% compared to corresponding weight values in the weighting table 200.

For another example, the compensation circuit 317 may configure a corresponding third weighting table (e.g., a weighting table 500 shown in FIG. 5) whose weight values are between that of the first weighting table and that of the second weighting table for users between the ages of 15 and 20 years old. In the embodiment of FIG. 5, weight values corresponding to respective sound level values in the weighting table 500 increase by 10% compared to the corresponding weight values in the weighting table 200.

For another example, the compensation circuit 317 may configure a corresponding fourth weighting table (e.g., a weighting table 600 shown in FIG. 6) whose weight values are different from that of the aforementioned first, second, and third weighting tables for users older than 30 years old. In the embodiment of FIG. 6, weight values corresponding to respective sound level values in the upper part of the weighting table 600 decrease by 15% compared to the corresponding weight values in the weighting table 200, but weight values corresponding to respective sound level values in the lower part of the weighting table 600 increase by 5% compared to the corresponding weight values in the weighting table 200.

The compensation circuit 317 may respectively configure corresponding weighting tables for other users of different ages.

In operations, the compensation circuit 317 may generate and transmit a weight adjustment instruction C-WT to the audio dose calculating circuit 113 according to the age of user of the audio processing device 100 to instruct the audio dose calculating circuit 113 to switch the weighting table utilized by the audio dose calculating circuit 113, so as to automatically adjust the contents of the weighting table utilized by the audio dose calculating circuit 113.

For example, when the user of the audio processing device 100 is younger than 15 years old, the compensation circuit 317 may utilize the weight adjustment instruction C-WT to instruct the audio dose calculating circuit 113 to calculate the audio dose value AD based on the contents of the weighting table 400.

For another example, when the user of the audio processing device 100 is between the age of 15 and 20 years old, the compensation circuit 317 may utilize the weight adjustment instruction C-WT to instruct the audio dose calculating circuit 113 to calculate the audio dose value AD based on the contents of the weighting table 500.

For another example, when the user of the audio processing device 100 is between 20 and 30 years old, the compensation circuit 317 may utilize the weight adjustment instruction C-WT to instruct the audio dose calculating circuit 113 to calculate the audio dose value AD based on the contents of the weighting table 200.

For another example, when the age of the user of the audio processing device 100 is older than 30 years old, the compensation circuit 317 may utilize the weight adjustment instruction C-WT to instruct the audio dose calculating circuit 113 to calculate the audio dose value AD based on the contents of the weighting table 600.

In other words, the audio dose calculating circuit 113 may automatically adjust the contents of the utilized weighting table in the situation when the age of the user of the audio processing device 100 is over a predetermined age (e.g., 15 years old) according to the instruction of the compensation circuit 317.

In practice, the compensation circuit 317 may utilize the aforementioned various approaches to determine the user's age. For the sake of brevity, those descriptions will not be repeated here.

In another embodiment, the aforementioned second target criterion refers to that a predetermined physiological indicator of the user of the audio processing device 100 exceeds a predetermined degree. For example, the compensation circuit 317 may utilize the weight adjustment instruction C-WT to instruct the audio dose calculating circuit 113 to calculate the audio dose value AD based on the contents of the weighting table 200 when the user's heart rate or blood pressure is normal, and may utilize the weight adjustment instruction C-WT to instruct the audio dose calculating circuit 113 to calculate the audio dose value AD based on the contents of the weighting table 500 when the user's heart rate or blood pressure increases by more than 20%. The compensation circuit 317 may utilize the weight adjustment instruction C-WT to instruct the audio dose calculating circuit 113 to calculate the audio dose value AD based on the contents of the weighting table 400 when the user's heart rate or blood pressure increases by more than 40%.

For another example, the compensation circuit 317 may utilize the weight adjustment instruction C-WT to instruct the audio dose calculating circuit 113 to calculate the audio dose value AD based on the contents of the weighting table 200 when the user's breathing rate is normal, and may utilize the weight adjustment instruction C-WT to instruct the audio dose calculating circuit 113 to calculate the audio dose value AD based on the contents of the weighting table 500 when the user's breathing rate increases by more than 15%. The compensation circuit 317 may utilize the weight adjustment instruction C-WT to instruct the audio dose calculating circuit 113 to calculate the audio dose value AD based on the contents of the weighting table 400 when the user's breathing rate increases by more than 50%.

In practice, the compensation circuit 317 may utilize the aforementioned various approaches to detect the user's predetermined physiological indicators. For the sake of brevity, those descriptions will not be repeated here.

In another embodiment, the aforementioned second target criterion refers to that the user of the audio processing device 100 is on a menstrual period. For example, the compensation circuit 317 may utilize the weight adjustment instruction C-WT to instruct the audio dose calculating circuit 113 to calculate the audio dose value AD based on the contents of the weighting table 400 or 500 when the user is on a menstrual period. The compensation circuit 317 may utilize the weight adjustment instruction C-WT to instruct the audio dose calculating circuit 113 to calculate the audio dose value AD based on the contents of the weighting table 200 after the user's menstrual period ends.

In practice, the compensation circuit 317 may utilize the aforementioned various approaches to determine whether the user is on a menstrual period or not. For the sake of brevity, those descriptions will not be repeated here.

In another embodiment, the aforementioned second target criterion refers to that the user of the audio processing device 100 is on a gestation period. For example, the compensation circuit 317 may utilize the weight adjustment instruction C-WT to instruct the audio dose calculating circuit 113 to calculate the audio dose value AD based on the contents of the weighting table 400, 500, or 600 when the user is on the gestation period. The compensation circuit 317 may utilize the weight adjustment instruction C-WT to instruct the audio dose calculating circuit 113 to calculate the audio dose value AD based on the contents of the weighting table 200 after the user gives birth.

In practice, the compensation circuit 317 may utilize the aforementioned various approaches to determine whether the user is on a gestation period or not. For the sake of brevity, those descriptions will not be repeated here.

In another embodiment, the aforementioned second target criterion refers to that an operating time of the audio processing device 100 is nighttime. For example, the compensation circuit 317 may utilize the weight adjustment instruction C-WT to instruct the audio dose calculating circuit 113 to calculate the audio dose value AD based on the contents of the weighting table 500 when the operating time of the audio processing device 100 is daytime, and may utilize the weight adjustment instruction C-WT to instruct the audio dose calculating circuit 113 to calculate the audio dose value AD based on the contents of the weighting table 200 or 600 when the operating time of the audio processing device 100 is nighttime.

In practice, the compensation circuit 317 may utilize the aforementioned various approaches to determine the operating time of the audio processing device 100. For the sake of brevity, those descriptions will not be repeated here.

In another embodiment, the aforementioned second target criterion refers to that an environmental temperature of the audio processing device 100 exceeds a predetermined magnitude. For example, the compensation circuit 317 may utilize the weight adjustment instruction C-WT to instruct the audio dose calculating circuit 113 to calculate the audio dose value AD based on the contents of the weighting table 200 when the environmental temperature of the audio processing device 100 is normal, and may utilize the weight adjustment instruction C-WT to instruct the audio dose calculating circuit 113 to calculate the audio dose value AD based on the contents of the weighting table 500 when the environmental temperature of the audio processing device 100 increases by more than 10%. The compensation circuit 317 may utilize the weight adjustment instruction C-WT to instruct the audio dose calculating circuit 113 to calculate the audio dose value AD based on the contents of the weighting table 400 when the environmental temperature of the audio processing device 100 increases by more than 20%

For another example, the compensation circuit 317 may utilize the weight adjustment instruction C-WT to instruct the audio dose calculating circuit 113 to calculate the audio dose value AD based on the contents of the weighting table 600 when the environmental temperature of the audio processing device 100 drops by more than 10%. The compensation circuit 317 may utilize the weight adjustment instruction C-WT to instruct the audio dose calculating circuit 113 to calculate the audio dose value AD based on the contents of the weighting table 500 when the environmental temperature of the audio processing device 100 drops by more than 20%.

In practice, the compensation circuit 317 may utilize the aforementioned various approaches to detect the environmental temperature of the audio processing device 100. For the sake of brevity, those descriptions will not be repeated here.

In another embodiment, the aforementioned second target criterion refers to that the user of the audio processing device 100 has changed, and the age difference between a new user and an original user exceeds a predetermined value. For example, if the audio dose calculating circuit 113 calculates the audio dose value AD corresponding to the original user of 18 years old based on the contents of the weighting table 500, then the compensation circuit 317 may utilize the weight adjustment instruction C-WT to instruct the audio dose calculating circuit 113 to calculate the audio dose value AD based on the contents of the weighting table 200 when the new user is more than ten years older than the original user.

For another example, the compensation circuit 317 may utilize the weight adjustment instruction C-WT to instruct the audio dose calculating circuit 113 to calculate the audio dose value AD based on the contents of the weighting table 600 when the new user is more than thirty years older than the original user.

For another example, the compensation circuit 317 may utilize the weight adjustment instruction C-WT to instruct the audio dose calculating circuit 113 to calculate the audio dose value AD based on the contents of the weighting table 400 when the new user is more than ten years younger than the original user.

In practice, the compensation circuit 317 may utilize the aforementioned various approaches to determine whether the user of the audio processing device 100 has changed or not, and to determine the age of the original user and the age of the new user. For the sake of brevity, those descriptions will not be repeated here.

In another embodiment, the aforementioned second target criterion refers to that the user of the audio processing device 100 has changed, and the sex of a new user is different from the sex of an original user. For example, if the audio dose calculating circuit 113 calculates the audio dose value AD corresponding to a male user based on the contents of the weighting table 200, then the compensation circuit 317 may utilize the weight adjustment instruction C-WT to instruct the audio dose calculating circuit 113 to calculate the audio dose value AD based on the contents of the weighting table 600 when the user of the audio processing device 100 changes from a male user to a female user.

For another example, the compensation circuit 317 may utilize the weight adjustment instruction C-WT to instruct the audio dose calculating circuit 113 to calculate the audio dose value AD based on the contents of the weighting table 200 when the user of the audio processing device 100 changes from a female user to a male user.

In practice, the compensation circuit 317 may utilize the aforementioned various approaches to determine whether the sex of the user of the audio processing device 100 has changed or not. For the sake of brevity, those descriptions will not be repeated here.

Then, the audio dose calculating circuit 113 may adopt the method of the embodiment of FIG. 1 as elaborated above to calculate the corresponding audio dose value AD based on the contents of the adjusted weighting table.

Therefore, the adjustment performed by the aforementioned compensation circuit 317 on the contents of the weighting table utilized by the audio dose calculating circuit 113 in the situation where the second target criterion is met is equivalent to adjusting the basis for calculating the audio dose value AD.

In some embodiments, the compensation circuit 317 may instruct the audio dose calculating circuit 113 to adjust the contents of the weighting table utilized by the audio dose calculating circuit 113 (i.e., to adjust the basis for calculating the audio dose value AD) when any one of the aforementioned second target criteria is met.

In other embodiments, the compensation circuit 317 instructs the audio dose calculating circuit 113 to adjust the contents of the weighting table utilized by the audio dose calculating circuit 113 only when two or more than two of the aforementioned second target criteria are met.

Please note that the contents of the aforementioned weighting tables 200, 400, 500, and 600 are merely some exemplary embodiments, rather than a restriction to the practical implementations. In practice, the quantity of rows in respective weighting table, the range of the sound level value, and/or the interval value of the sound level value may be instead designed to be different from those in the aforementioned embodiments.

As can be appreciated from the foregoing descriptions, the compensation circuit 317 may adaptively adjust the basis for calculating the audio dose value AD based on differences in the user's own physiological condition, differences between users, differences in environmental temperature, and/or differences in time of use, thereby consequentially affecting the results of comparing the audio dose value AD with the corresponding dose threshold performed by the control circuit 116. Such approach not only significantly improves the flexibility of use and the application scope of the audio dose monitoring circuit 110, but also renders the audio dose monitoring circuit 110 and the audio processing device 100 to better meet the needs of different users, and/or different usage scenarios.

From another aspect, the structure and operations of the aforementioned audio dose monitoring circuit 110 can offer the user an adaptive hearing protection that is more customized and can be automatically adapted in response to different conditions.

In addition, the structure and operations of the aforementioned audio dose monitoring circuit 110 can also enable the audio processing device 100 to support applications shared by multiple users, which significantly increases the application value of the audio processing device 100.

In practice, the aforementioned compensation circuit 317 may be realized with various micro-processors, micro-controllers, digital processing circuits, digital signal processing circuits, or ASICs. In some embodiments, the compensation circuit 317 may be integrated with the audio dose calculating circuit 113, or the compensation circuit 317 may be integrated with the control circuit 116.

The foregoing descriptions regarding the connections, implementations, operations, and related advantages of other components in FIG. 1 are also applicable to those in FIG. 3. For the sake of brevity, those descriptions will not be repeated here.

Please note that the structure of the audio processing device 100 in the aforementioned embodiments of FIG. 1 and FIG. 3 is merely an exemplary embodiment, rather than a restriction to the practical implementations. In some embodiments, for example, one of the main microphone 130, the in-ear microphone 140, the audio playback device 120, and the prompt device 150 may be omitted.

For another example, in some embodiments, the main microphone 130 and the in-ear microphone 140 may be omitted.

For another example, in some embodiments, the main microphone 130 and the audio playback device 120 may be omitted.

For another example, in some embodiments, the in-ear microphone 140 and the audio playback device 120 may be omitted.

In addition, in some embodiments, the aforementioned compensation circuit 317 may only compensate the multiple sound level values SVs generated by the sound level measuring circuit 111, and does not adjust the contents of the weighting table utilized by the audio dose calculating circuit 113. Alternatively, the compensation circuit 317 may only adjust the contents of the weighting table utilized by the audio dose calculating circuit 113, and does not compensate the multiple sound level values SVs generated by the sound level measuring circuit 111.

In addition, in some embodiments, when the aforementioned compensation circuit 317 instructs the sound level measuring circuit 111 to add the aforementioned compensation amount to the sound level values SV to form compensated sound level values SV', the compensation circuit 317 may instruct the sound level measuring circuit 111 to only compensate each sound level value SV related to the main microphone 130 (e.g., a sound level value SV originated from the aforementioned first sound level value) or related to the in-ear microphone 140 (e.g., a sound level value SV originated from the aforementioned second sound level value), but not to compensate the sound level value SV related to the audio playback device 120 (e.g., the sound level value SV originated from the aforementioned third sound level value generated by the control circuit 116).

Certain terms are used throughout the description and the claims to refer to particular components. One skilled in the art appreciates that a component may be referred to as different names. This disclosure does not intend to distinguish between components that differ in name but not in function. In the description and in the claims, the term "comprise" is used in an open-ended fashion, and thus should be interpreted to mean "include, but not limited to." The term "couple" is intended to compass any indirect or direct connection. Accordingly, if this disclosure mentioned that a first device is coupled with a second device, it means that the first device may be directly or indirectly connected to the second device through electrical connections, wireless communications, optical communications, or other signal connections with/without other intermediate devices or connection means.

The term "and/or" may comprise any and all combinations of one or more of the associated listed items. In addition, the singular forms "a," "an," and "the" herein are intended to comprise the plural forms as well, unless the context clearly indicates otherwise.

Other embodiments of the invention will be apparent to those skilled in the art from consideration of the specification and practice of the invention disclosed herein. It is intended that the specification and examples be considered as exemplary only, with a true scope and spirit of the invention indicated by the following claims.

What is claimed is:

1. An audio processing device (100), comprising:
   an audio playback device (120), arranged to operably generate sound based on an audio configuration signal (ACS); and
   an audio dose monitoring circuit (110), comprising:
      a sound level measuring circuit (111), arranged to operably generate multiple sound level values (SVs) respectively corresponding to multiple sound levels based on the audio configuration signals (ACSs), wherein the multiple sound levels are generated by the audio playback device (120) at multiple time points;

an audio dose calculating circuit (113), coupled with the sound level measuring circuit (111), and arranged to operably generate an audio dose value (AD) corresponding to a measuring period based on the multiple sound level values (SVs) and contents of a weighting table (200);

a control circuit (116), coupled with the audio dose calculating circuit (113), and arranged to operably generate the audio configuration signal (ACS), and to operably compare the audio dose value (AD) with a dose threshold to determine whether to generate a control signal (CTL) or not; and an indication signal generating circuit (114), coupled with the control circuit (116), and arranged to operably generate a corresponding indication signal (INS) according to the control signal (CTL);

wherein the control circuit (116) generates the control signal (CTL) when the audio dose value (AD) exceeds the dose threshold, and the control circuit (116) is further arranged to operably switch a magnitude of the dose threshold when a predetermined criterion is met.

2. The audio processing device (100) of claim 1, wherein the predetermined criterion is selected from a group consisting of following criteria:

an age of a user of the audio processing device (100) is over a predetermined age;

a change in a predetermined physiological indicator of the user of the audio processing device (100) exceeds a predetermined degree;

the user of the audio processing device (100) is on a menstrual period;

the user of the audio processing device (100) is on a gestation period;

an operating time of the audio processing device (100) is nighttime;

a change in an environmental temperature of the audio processing device (100) exceeds a predetermined magnitude;

the user of the audio processing device (100) has changed, and an age difference between a new user and an original user exceeds a predetermined value; and the user of the audio processing device (100) has changed, and the sex of a new user is different from the sex of an original user.

3. The audio processing device (100) of claim 1, wherein the audio dose calculating circuit (113) respectively converts the multiple sound level values (SVs) into corresponding multiple weight values based on the contents of the weighting table (200), and respectively multiplies the multiple weight values by multiple corresponding unit time lengths, so as to generate multiple weighted values, wherein a sum of the multiple unit time lengths equals a total time length of the measuring period;

wherein the audio dose calculating circuit (113) further calculates a sum of the multiple weighted values, and utilizes the sum to be the audio dose value (AD) corresponding to the measuring period.

4. The audio processing device (100) of claim 1, wherein the audio dose monitoring circuit (110) further comprises:

a transmission circuit (115), coupled with the indication signal generating circuit (114), and arranged to operably transmit the indication signal (INS) to a prompt device (150).

5. An audio processing device (100), comprising:
a microphone (130; 140), arranged to operably receive sound; and an audio dose monitoring circuit (110), comprising:

a sound level measuring circuit (111), arranged to operably generate multiple sound level values (SVs) respectively corresponding to sound levels received by the microphone (130; 140) at multiple time points;

an audio dose calculating circuit (113), coupled with the sound level measuring circuit (111), and arranged to operably generate an audio dose value (AD) corresponding to a measuring period based on the multiple sound level values (SVs) and contents of a weighting table (200);

a control circuit (116), coupled with the audio dose calculating circuit (113), and arranged to operably compare the audio dose value (AD) with a dose threshold to determine whether to generate a control signal (CTL) or not; and an indication signal generating circuit (114), coupled with the control circuit (116), and arranged to operably generate a corresponding indication signal (INS) according to the control signal (CTL);

wherein the control circuit (116) generates the control signal (CTL) when the audio dose value (AD) exceeds the dose threshold, and the control circuit (116) is further arranged to operably switch a magnitude of the dose threshold when a predetermined criterion is met.

6. The audio processing device (100) of claim 5, wherein the predetermined criterion is selected from a group consisting of following criteria:

an age of a user of the audio processing device (100) is over a predetermined age;

a change in a predetermined physiological indicator of a user of the audio processing device (100) exceeds a predetermined degree;

the user of the audio processing device (100) is on a menstrual period;

the user of the audio processing device (100) is on a gestation period;

an operating time of the audio processing device (100) is nighttime;

a change in an environmental temperature of the audio processing device (100) exceeds a predetermined magnitude;

the user of the audio processing device (100) has changed, and an age difference between a new user and an original user exceeds a predetermined value; and the user of the audio processing device (100) has changed, and the sex of a new user is different from the sex of an original user.

7. The audio processing device (100) of claim 5, wherein the audio dose calculating circuit (113) respectively converts the multiple sound level values (SVs) into corresponding multiple weight values based on the contents of the weighting table (200), and respectively multiplies the multiple weight values by multiple corresponding unit time lengths, so as to generate multiple weighted values, wherein a sum of the multiple unit time lengths equals a total time length of the measuring period;

wherein the audio dose calculating circuit (113) further calculates a sum of the multiple weighted values, and utilizes the sum to be the audio dose value (AD) corresponding to the measuring period.

8. The audio processing device (100) of claim 5, wherein the audio dose monitoring circuit (110) further comprises:
 a transmission circuit (115), coupled with the indication signal generating circuit (114), and arranged to operably transmit the indication signal (INS) to a prompt device (150).

\* \* \* \* \*